US009788719B2

(12) United States Patent
Makihira et al.

(10) Patent No.: US 9,788,719 B2
(45) Date of Patent: Oct. 17, 2017

(54) FUNDUS IMAGING APPARATUS AND METHOD

(71) Applicant: CANON KABUSHIKI KAISHA, Tokyo (JP)

(72) Inventors: Tomoyuki Makihira, Tokyo (JP); Kazuhide Miyata, Yokohama (JP); Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 241 days.

(21) Appl. No.: 13/767,096

(22) Filed: Feb. 14, 2013

(65) Prior Publication Data

US 2013/0215387 A1   Aug. 22, 2013

(30) Foreign Application Priority Data

Feb. 21, 2012 (JP) ................. 2012-035316

(51) Int. Cl.
    *A61B 3/14* (2006.01)
    *A61B 3/10* (2006.01)

(52) U.S. Cl.
    CPC .............. *A61B 3/14* (2013.01); *A61B 3/1025* (2013.01)

(58) Field of Classification Search
    CPC ......... A61B 3/113; A61B 3/12; A61B 3/1025; A61B 3/1208; A61B 3/1216; A61B 3/1225; A61B 3/1233; A61B 3/1241; A61B 3/14; A61B 3/145; G02B 27/0093
    USPC ............... 351/206, 209, 210, 220, 221, 246; 396/18, 51; 356/2, 450–521, 601–624
    See application file for complete search history.

(56) References Cited

U.S. PATENT DOCUMENTS

| | | | |
|---|---|---|---|
| 6,337,920 B1 | 1/2002 | Mühlhoff | |
| 7,758,189 B2 | 7/2010 | Hammer et al. | |
| 8,204,300 B2 | 6/2012 | Sugita et al. | |
| 8,384,908 B2 | 2/2013 | Sugita et al. | |
| 8,390,818 B2 | 3/2013 | Hirose et al. | |
| 2007/0252951 A1* | 11/2007 | Hammer | A61F 9/008 351/221 |
| 2009/0285354 A1 | 11/2009 | Hirose et al. | |
| 2011/0155916 A1 | 6/2011 | Furusawa et al. | |
| 2011/0267581 A1* | 11/2011 | Nakajima | A61B 3/102 351/206 |

(Continued)

FOREIGN PATENT DOCUMENTS

| | | |
|---|---|---|
| JP | 11-123178 A | 5/1999 |
| JP | 2010-201102 A | 9/2010 |

(Continued)

*Primary Examiner* — Ricky Mack
*Assistant Examiner* — Gary O'Neill
(74) *Attorney, Agent, or Firm* — Fitzpatrick, Cella, Harper & Scinto

(57) ABSTRACT

In order to suppress a load on a subject when a fundus is irradiated with multiple beams, a fundus imaging apparatus for forming an image of a first area in the object, includes: a determination unit for determining a second area other than the first area in the object to be inspected; a detection unit for detecting moving of the object to be inspected on the basis of return light from the second area, which is irradiated with second light; a correction unit for correcting the first area on the basis of the detected moving; and a forming unit for forming an image of the object to be inspected on the basis of the return light from the corrected first area, which is irradiated with the first light.

21 Claims, 11 Drawing Sheets

(56) References Cited

U.S. PATENT DOCUMENTS

| | | |
|---|---|---|
| 2011/0301455 A1 | 12/2011 | Numajiri et al. |
| 2012/0002166 A1 | 1/2012 | Tomatsu et al. |
| 2012/0019780 A1 | 1/2012 | Nozato |
| 2012/0154746 A1 | 6/2012 | Nozato |
| 2012/0154747 A1 | 6/2012 | Makihira |
| 2012/0229761 A1 | 9/2012 | Makihira |
| 2012/0229762 A1 | 9/2012 | Makihira |
| 2012/0229763 A1 | 9/2012 | Suehira et al. |
| 2012/0229764 A1 | 9/2012 | Tomatsu et al. |
| 2012/0229765 A1 | 9/2012 | Makihira |
| 2012/0249957 A1* | 10/2012 | Shibata et al. ............... 351/206 |
| 2012/0320338 A1 | 12/2012 | Hirose et al. |
| 2012/0327365 A1 | 12/2012 | Makihira |
| 2013/0010258 A1 | 1/2013 | Utagawa |
| 2013/0016320 A1 | 1/2013 | Naba |
| 2013/0070988 A1 | 3/2013 | Makihira |

FOREIGN PATENT DOCUMENTS

| | | |
|---|---|---|
| JP | 2010-279576 A | 12/2010 |
| JP | 2011-212206 A | 10/2011 |

* cited by examiner

FUNDUS IMAGING APPARATUS AND METHOD

BACKGROUND OF THE INVENTION

Field of the Invention

The present invention relates to a fundus imaging apparatus and a method, and, more particularly, to a method and fundus imaging apparatus for scanning a fundus with irradiation light to obtain a fundus image.

Description of the Related Art

In recent years, as devices for imaging a fundus, the use of a fundus imaging apparatus for scanning with irradiation light to photograph or image the fundus, such as confocal scanning laser opthalmoscope (SLO) for acquiring a still or moving image of high resolution, has been popular. In such fundus imaging apparatus, some time is required from when imaging is started until when the imaging is complete. Therefore, the imaging is susceptible to involuntary eyeball movements called flicks, eyeball movements due to poor fixation, or moving of an eye accompanying moving of the face, which adds more importance to fundus tracking for tracking moving of a fundus (U.S. Pat. No. 7,758,189).

In the configuration disclosed in U.S. Pat. No. 7,758,189, the fundus is irradiated with multiple beams for imaging and tracking the fundus, and hence a load on the eye to be inspected has been heavy.

SUMMARY OF THE INVENTION

The present invention is to provide a fundus imaging apparatus and method capable of acquiring a fundus image with small effects of eyeball movements while suppressing a load on an eye to be inspected.

In order to solve the above-mentioned problem, a fundus imaging apparatus according to an exemplary embodiment of the present invention for imaging an object to be inspected on the basis of the return light from a first area in the object to be inspected, which is irradiated with first light, includes: a determination unit for determining a second area other than the first area in the object to be inspected; a detection unit for detecting moving of the object to be inspected on the basis of return light from the second area, which is irradiated with second light; a correction unit for correcting the first area on the basis of the detected moving; and a forming unit for forming an image of the object to be inspected on the basis of the return light from the corrected first area, which is irradiated with the first light.

According to the exemplary embodiment of the present invention, a fundus image with small effects of eyeball movements may be acquired while suppressing the load on the eye to be inspected.

Further features of the present invention will become apparent from the following description of exemplary embodiments with reference to the attached drawings.

DESCRIPTION OF THE EMBODIMENTS

Embodiments of the present invention are described in detail with reference to the drawings.

First Embodiment

Now, a first embodiment of the present invention is described.

In this embodiment, description is given of an example in which a first fundus imaging apparatus is used as a tracking apparatus, a second fundus imaging apparatus is used as an adaptive optics (AO)-SLO apparatus, a beam of the tracking apparatus and a beam of the AO-SLO apparatus enter a fundus simultaneously, and tracking data is reflected on the AO-SLO apparatus, to thereby acquire a stable and high-quality AO-SLO image.

(Overall Configuration of Apparatus)

Figure 1:
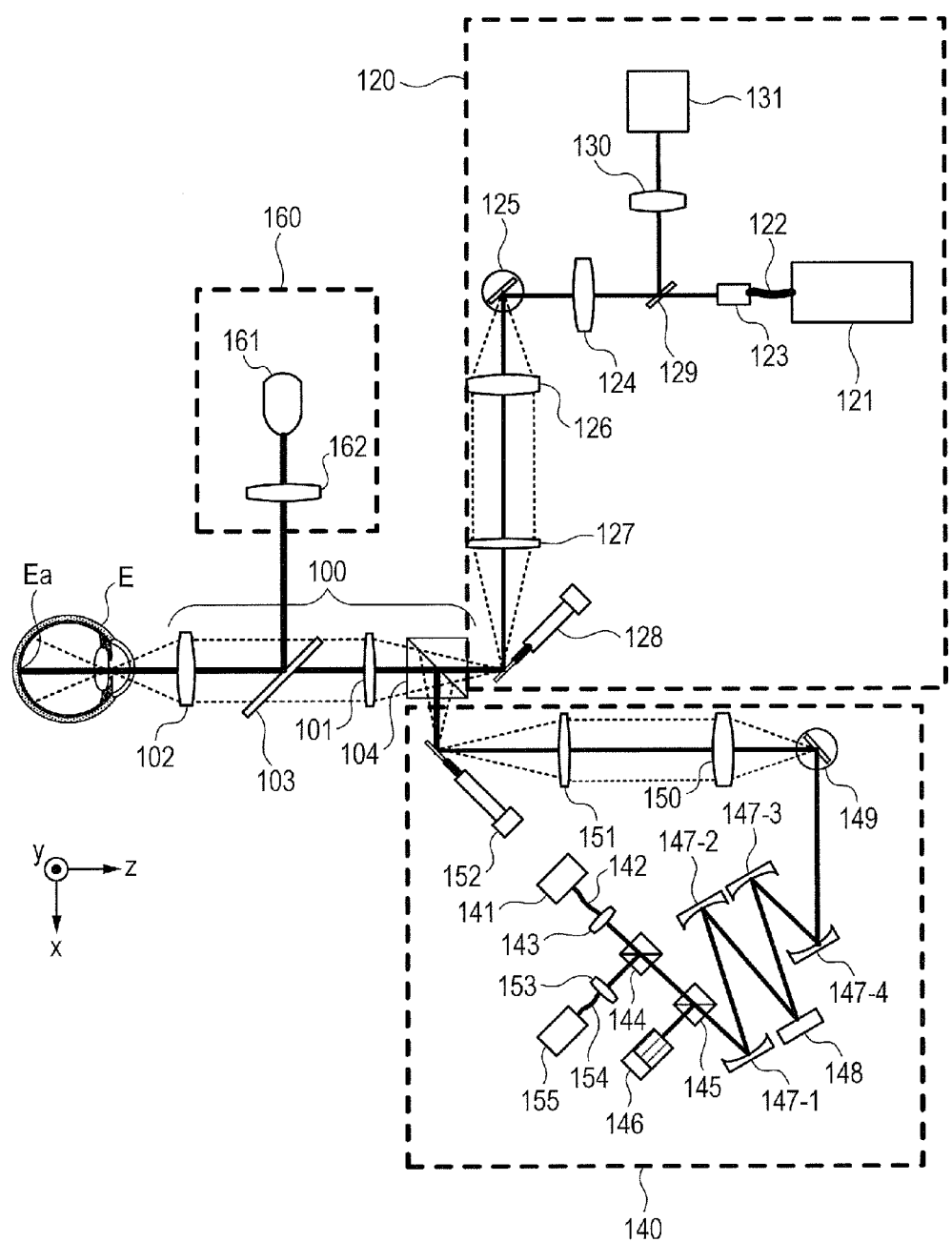
FIG. 1 is a schematic diagram of a configuration of a fundus imaging apparatus according to a first embodiment.

The fundus imaging apparatus according to this embodiment is described with reference to an optical schematic diagram of FIG. 1.

The fundus imaging apparatus used in this embodiment includes the first fundus imaging apparatus, the second fundus imaging apparatus, and an internal fixation target apparatus.

The first fundus imaging apparatus includes an ocular lens unit 100 and an SLO 120. A laser light source 121 may suitably be a semiconductor laser or a super luminescent diode (SLD) light source. In order to reduce the brightness of a subject and maintain the resolution for fundus observation, the wavelength to be used is suitably a near infrared wavelength range of 700 nm to 1,000 nm. In this embodiment, a semiconductor laser having a wavelength of 780 nm is used. Light emitted from the laser light source 121 is transmitted through a fiber 122 to be emitted from a fiber collimator 123 as a collimated beam (measuring light).

The emitted light is guided to an SLO scanner (X) 128 through a lens 124, an SLO scanner (Y) 125, and relay lenses 126 and 127. The beam is further transmitted through a scan lens 101 and an ocular lens 102 to enter an eye to be inspected E. In this embodiment, galvano scanners are used as the SLO scanners (X) 128 and (Y) 125.

Z, x, and y coordinates to be used in this embodiment correspond to an eye axis direction, and a horizontal direction and a vertical direction with respect to a fundus image, respectively. In this embodiment, the x direction corresponds to a main scanning direction, and the y direction corresponds to a sub scanning direction.

The beam that has entered the eye to be inspected E irradiates a fundus Ea of the eye to be inspected E as a spot beam. This beam is reflected or scattered by the fundus Ea of the eye to be inspected E and follows the same optical path to return to a ring mirror 129. Of the light that irradiates the fundus Ea and is back-scattered, the light that has passed through a portion around the pupil (reflected light) is reflected by the ring mirror 129 and received by an avalanche photodiode (hereinafter referred to as APD) 131 through a lens 130.

Similarly to the first fundus imaging apparatus, the second fundus imaging apparatus includes the ocular lens unit 100 and an AO-SLO unit 140 having an AO apparatus. As a light source 141, an SLD light source having a wavelength of 840 nm is used. In this embodiment, the light source is shared for imaging the fundus and for measuring a wavefront, but a configuration may be adopted in which separate light sources are used and light beams are combined in the course of the optical path.

The light emitted from the light source 141 is transmitted through a fiber 142 to be radiated from a fiber collimator 143 as collimated measuring light. The radiated measuring light is transmitted through a beam splitter 144 and guided to a compensation optical system.

The compensation optical system includes a beam splitter 145, a wavefront sensor 146 for measuring aberration, a wavefront correction device 148, and reflection mirrors 147-1 to 147-4 for guiding the light to those components. The reflection mirrors 147-1 to 147-4 are arranged so that at least the eye to be inspected E and each of the wavefront sensor 146 and the wavefront correction device 148 have an optically conjugate relationship. Further, in this embodiment, a spatial phase modulator using a liquid crystal element is used as the wavefront correction device 148.

The measuring light enters the wavefront correction device 148 to be reflected thereby, and is emitted to the reflection mirror 147-3. Similarly, the light that has returned from the fundus Ea of the eye to be inspected E also enters the wavefront correction device 148, and is then emitted to the reflection mirror 147-2. Further, the measuring light is scanned two-dimensionally by an AO-SLO scanner (X) 149 and an AO-SLO scanner (Y) 152. In this embodiment, a high-speed resonance scanner (scanner for main scanning) is used as the AO-SLO scanner (X) 149, and a galvano scanner (scanner for sub scanning) is used as the AO-SLO scanner (Y) 152.

The measuring light scanned by the AO-SLO scanners (X) 149 and (Y) 152 is reflected by a beam splitter 104 and transmitted through the scan lens 101 and the ocular lens 102 to enter the eye to be inspected E. The measuring light that has entered the eye to be inspected E is reflected or scattered by the fundus Ea and follows the same optical path, and the beam splitter 145 allows a part of the measuring light to enter the wavefront sensor 146. The wavefront sensor 146 measures a wavefront of the beam, and a Shack-Hartmann sensor is used as the wavefront sensor 146. A part of the reflected/scattered light that has transmitted through the beam splitter 145 is then reflected by the beam splitter 144 and guided to a light intensity sensor 155 including a photomultiplier tube (PM) through a fiber collimator 153 and a fiber 154.

The guided light is converted to an electric signal in the light intensity sensor 155 and subjected to imaging processing by a control portion (not shown). Then, when the control portion rotates the resonance scanner as the AO-SLO scanner (X) 149 and the galvano scanner as the AO-SLO scanner (Y) 152 by a minute angle (which means an angle smaller than a scan angle of the SLO 120), light intensity information from an area to be imaged of the fundus Ea is obtained, and an image is constructed as the fundus image to be displayed on a display device (see FIG. 2) under the control of the control portion.

Further, the wavefront sensor 146 and the wavefront correction device 148 are connected to the control portion. The control portion calculates, on the basis of the wavefront acquired by the measurement result of the wavefront sensor 146, such modulation amount (correction amount) as to correct the wavefront to that without the aberration, and instructs the wavefront correction device 148 to perform the modulation. The measurement of the wavefront and instruction to the wavefront correction device 148 are repeatedly processed, with the result that feedback control is performed so that an optimal wavefront is always obtained. In this embodiment, a reflective liquid crystal spatial phase modulator of 600×600 pixels is used as the wavefront correction device 148.

An internal fixation target 160 includes a light source 161 and a lens 162. As the light source 161, multiple light emitting diodes (LD) arranged in matrix are used. A turn-on position of the light emitting diodes is changed under the control of the control portion in accordance with the part desired to be imaged. Light from the light source 161 is guided to the eye to be inspected E by a dichroic mirror 103 via the lens 162. The light emitted from the light source 161 is 520 nm, and a desired pattern is displayed by the control portion.

(Functional Configuration)

Figure 2:
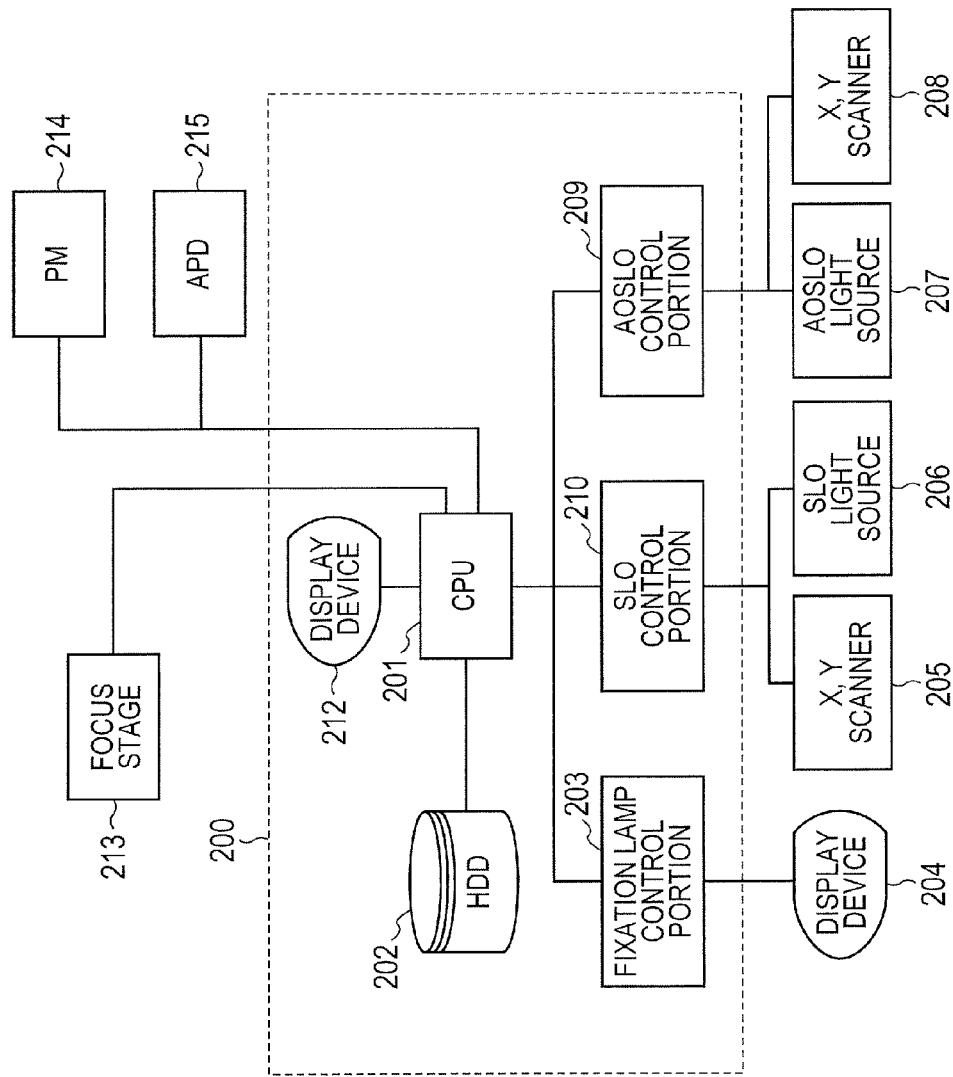
FIG. 2 is a functional schematic diagram of the fundus imaging apparatus according to the first embodiment.

A functional configuration according to this embodiment is described with reference to FIG. 2. A control portion (PC) 200 for controlling functional members includes a display device 212, a CPU 201, a storage device HDD 202, and a fixation target control portion 203, an SLO control portion 210, and an AO-SLO control portion 209, which are control portions for the respective apparatus. Under instructions from the CPU 201, a display device 204 (corresponding to the light source 161 of FIG. 1) for displaying the fixation target, an X, Y scanner 205 (corresponding to the SLO scanners 125 and 128 of FIG. 1) and an SLO light source 206 (corresponding to the laser light source 121 of FIG. 1) of the SLO apparatus, and an X, Y scanner 208 (corresponding to the AO-SLO scanners 149 and 152 of FIG. 1) and an AO-SLO light source 207 (corresponding to the light source 141 of FIG. 1) of the AO-SLO apparatus are operated under the control of the fixation target control portion 203, the SLO control portion 210, and the AO-SLO control portion 209, respectively.

Further, a signal from the eye to be inspected E is obtained via a PM 214 (corresponding to the light intensity sensor 155 of FIG. 1), which is a light receiving member of the AO-SLO apparatus, and an APD 215 (corresponding to the APD 131 of FIG. 1), which is a light receiving member of the SLO apparatus. The obtained signal is imaged by the CPU 201 and displayed on the display device 212.

(Flow)

Figure 3:
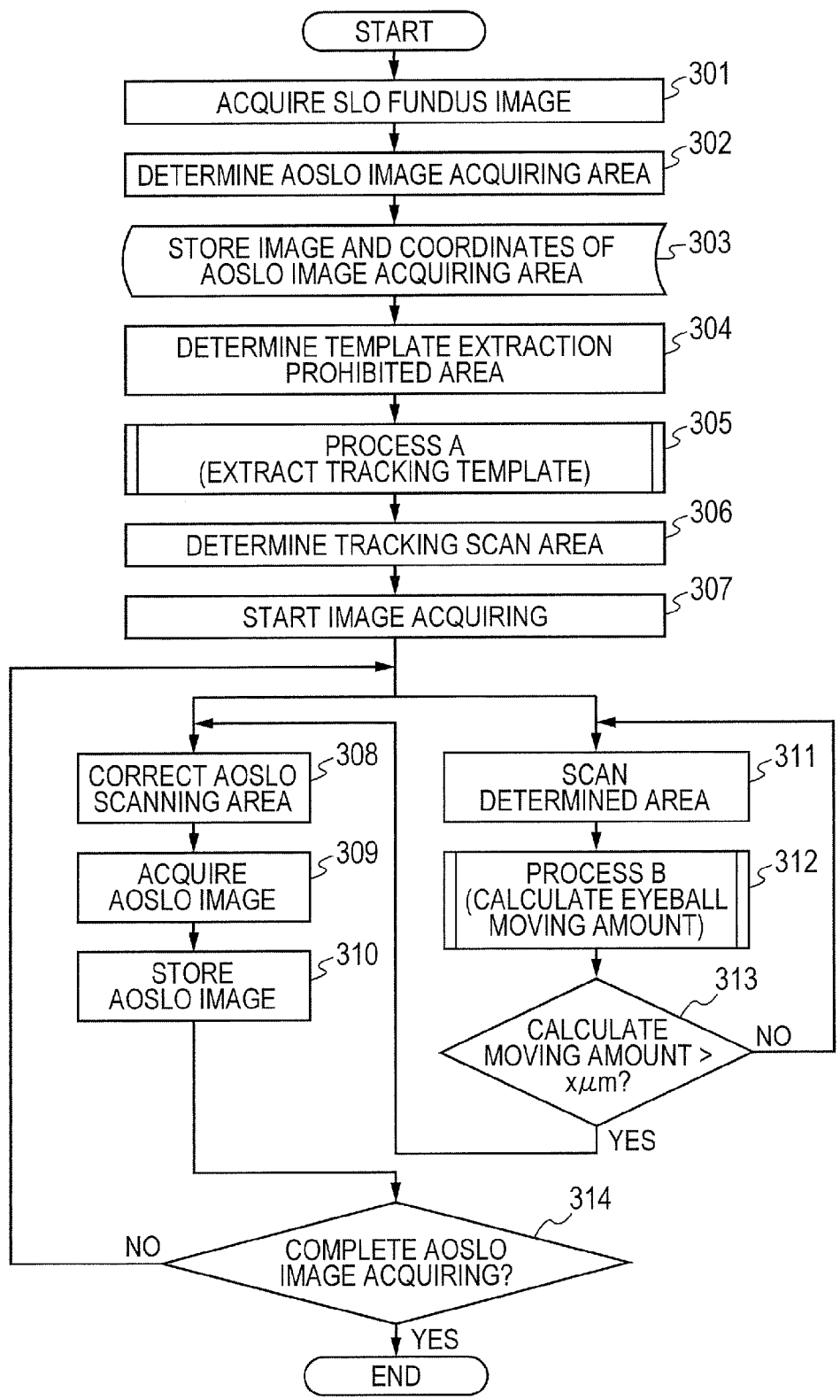
FIG. 3 is a schematic flowchart of a procedure according to the first embodiment.

With the above-mentioned apparatus, the SLO apparatus as the first fundus imaging apparatus is used for tracking and the tracking result is fed back to the scanners of the AO-SLO apparatus, to thereby acquire the AO-SLO image of a desired position stably. A flow thereof is illustrated in FIG. 3. Note that, unless otherwise noted, the processing is executed by the CPU 201.

First, the first fundus imaging apparatus acquires an SLO fundus image by outputting a laser from the laser light source 121 and receiving the reflected light by the APD 131 in a state in which the fixation target 161 is turned on to be presented to the eye to be inspected E (Step 301). The first fundus imaging apparatus functions as a unit for taking a fundus image of the entire fundus of the eye to be inspected.

On the basis of an instruction by an operator from an input device (not shown), an AO-SLO image acquiring area is determined in the SLO image (Step 302). This processing is executed by a module area that functions in the CPU 201 as an area setting unit for setting a first area of the eye to be inspected, which is irradiated with AO-SLO light as a first beam. The first area is set on the basis of the fundus image acquired in advance. The set area to be imaged with the AO-SLO light is stored in a memory of the CPU 201 (Step 303).

A certain set area from the AO-SLO image acquiring area is set as a prohibited area of acquisition of the SLO image (Step 304). More specifically, an area obtained by adding a predetermined amount to the first area to thereby add an area of a predetermined width to the periphery of the first area is set as the prohibited area of the acquisition of the SLO image. Outside the prohibited area of the acquisition of the SLO image, at least one template for tracking is extracted (process A: Step 305). Specifically, on the basis of the first area set by the area setting unit, in an area except for or other than the prohibited area of the acquisition of the SLO image, a second area of the eye to be inspected, which is to be irradiated with SLO light for tracking as a second beam, is set and extracted as the template. The setting and determination of the second area are executed by a module area that functions in the CPU 201 as a determination unit. A certain area around the extracted template is determined as a tracking scan area (Step 306).

Imaging for the fundus image for diagnosis is started (Step 307), and the AO-SLO apparatus and the SLO apparatus are operated. The AO-SLO apparatus drives the X, Y scanner 208 to scan the image acquiring area determined in Step 302 (Step 308), and an AO-SLO signal is acquired to be imaged (Step 309). Specifically, on the basis of return light of the AO-SLO light as the first beam, an AO-SLO image as a first image of the eye to be inspected is formed. The image formation is executed by a module area that functions in the CPU 201 as a forming unit. As described below, the forming unit forms the image of the eye to be inspected on the basis of the return light from the corrected first area, which is irradiated with first light. Thereafter, the AO-SLO image is stored in the HDD 202 (Step 310).

At the same time, the X, Y scanner 205 of the SLO apparatus is used to scan the area determined in Step 306 (Step 311), to thereby acquire the SLO image. Specifically, on the basis of return light of the above-mentioned second beam from the eye to be inspected, a second image of the eye to be inspected for tracking is formed. It is preferred that the formation of the image be executed by a module area that functions in the CPU 201 as a forming unit for detecting moving, and that a detection unit for detecting moving of the eye to be inspected use thus-obtained multiple images for detecting moving and detect the moving of the eye to be inspected on the basis of the images.

Template matching is executed in the acquired SLO image and coordinates of the template are compared with matching coordinates to calculate eyeball moving (moving amount and direction) (process B: Step 312). This calculation processing is executed by a module area that functions in the CPU 201 as the detection unit for detecting the moving of the eye to be inspected on the basis of the second image. In other words, the detection unit detects the moving of the eye to be inspected on the basis of the return light from the second area, which is irradiated with second light. Note that the detection unit detects the moving by comparing a characteristic image extracted as the template with a newly-formed second image, which has been obtained at this stage, and includes a unit for detecting the moving of the eye to be inspected that is subjected to the comparison. In other words, the detection unit further includes a unit for extracting the characteristic image from a first image for detecting moving of multiple images for detecting moving, and detects the moving of the eye to be inspected by comparing a newly-formed second image for detecting moving with the characteristic image.

In this case, when the moving amount does not exceed a defined value (x), the processing returns to Step 311, and when the moving amount exceeds the defined value, the moving amount is reflected in driving the scanner of the AO-SLO apparatus (Yes in Step 313). This correction of the first area by driving the scanner is performed on the basis of the detected moving of the eye to be inspected, and the processing is executed by a module area that functions in the CPU 201 as a correction unit for correcting the first area. Further, the correction unit performs the correction by correcting a scan area of the scanner as a scanning unit in this embodiment. Note that, the scanning unit irradiates and scans the first area with the first light, and the above-mentioned correction unit corrects the scan area in the scanning unit to correct the first area. When the AO-SLO imaging is complete, the processing is ended (Yes in Step 314).

Figure 4A:
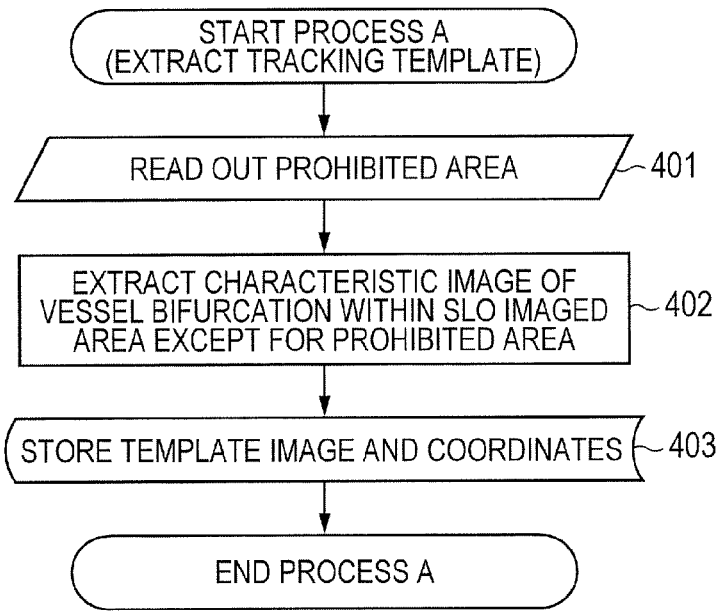
FIG. 4A is a schematic flowchart of a detailed procedure of a process A according to the first embodiment.

The process A of Step 305 is described with reference to FIG. 4A. The SLO image and the prohibited area of the acquisition of the SLO image are read out (Step 401). The template is extracted from the SLO image other than the prohibited area (Step 402). The template coordinates and image are stored in the memory (Step 403).

Figure 4B:
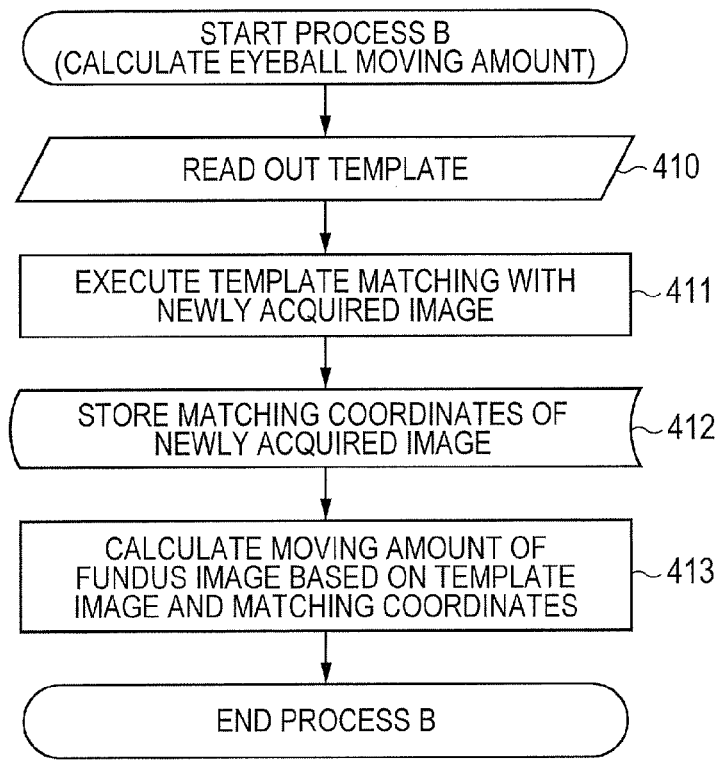
FIG. 4B is a schematic flowchart of a detailed procedure of a process B according to the first embodiment.

The process B is described with reference to FIG. 4B. The template image and coordinates are read out from the memory (Step 410). The read-out template image and a newly acquired SLO image are used to execute the template matching (Step 411). Matching image and coordinates found as a result of the matching are stored in the memory (Step 412). The moving (moving amount and direction) of the fundus is calculated based on the template coordinates and the matching coordinates (Step 413).

Specific Example

Figure 5A:
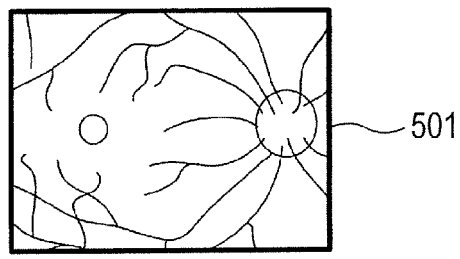
FIGS. 5A, 5B, 5C, 5D, 5E and 5F are explanatory diagrams of specific fundus images according to the first embodiment.

A specific example is described with reference to FIGS. 5A to 5F. The first fundus imaging apparatus causes a beam of 780 nm to enter the retinal fundus, and uses the galvano scanners 125 and 128 to scan an area of 10 mm×8 mm on the fundus with a spot diameter of 20 µm. A signal obtained by the APD 131 is imaged by the PC 200. FIG. 5A is a schematic diagram of the acquired SLO image. In an obtained SLO image 501, the macula, the optic disc, and a vascular image may be observed.

Figure 5B:
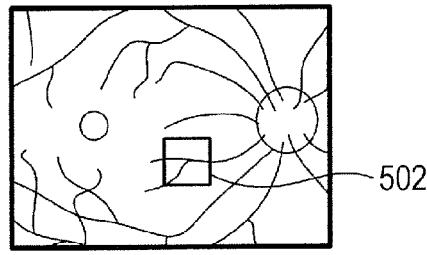
Figure 5C:
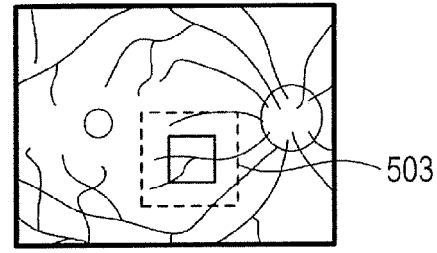
Figure 5D:
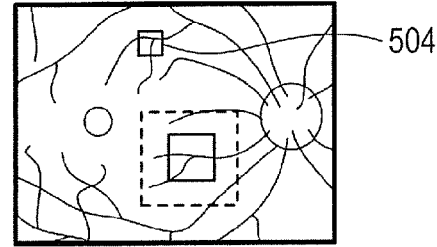

As illustrated in FIG. 5B, an image area 502 as the first area desired to be acquired by the AO-SLO apparatus as the second fundus imaging apparatus is determined as specified by the operator. The AO-SLO image acquiring area is generally 3 mm×3 mm or smaller. The AO-SLO light source has a wavelength of 840 nm±50 nm and a spot diameter of 5 µm at the fundus. In other words, the resolution of the AO-SLO image as the first image is higher than the resolution of the SLO image as the second image. The scan area of the AO-SLO apparatus here is about 1 mm×1 mm on the fundus. Next, in order to place no load on the eye to be inspected, an area 503 in FIG. 5C of 1 mm as the predetermined amount in the periphery of the AO-SLO image acquiring area plus 1 mm in which the eyeball moves during the imaging, and hence an area of a total of 2 mm, is specified as a tracking template extraction prohibited area.

Next, in order to perform tracking, a template is extracted from the SLO image 501. In the extraction, the template is extracted within the area of the SLO image 501 other than the area 503. Like an area 504 of FIG. 5D, an area image of a vessel bifurcation area is extracted as the template from a template image 504 as the second image. This processing is executed by a module area that functions in the CPU 201 as a unit for extracting a characteristic area image from the second image. The size of the template is 0.5 mm×0.5 mm.

Figure 5E:
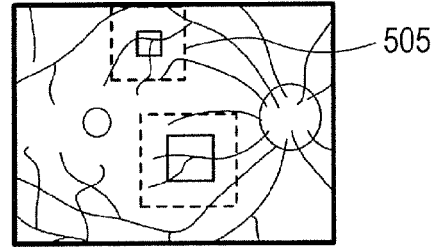

The template moves with eyeball movements, and hence with the addition of 1 mm to the periphery of the template, a scan area 505 of FIG. 5E is 1.5 mm×1.5 mm.

Figure 5F:
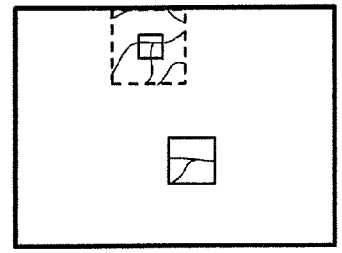

When the AO-SLO image is actually acquired while tracking is performed, only the tracking scan area 505 and the AO-SLO image are obtained as in FIG. 5F. The acquired SLO image is searched for the same image as the extracted template image 504. An image area with the highest match rate is identified and compared with the template coordinates to calculate the moving of the fundus. With the tracking speed being 100 Hz and the acquisition speed of the AO-SLO image being 50 Hz, the AO-SLO image is acquired by performing control so that the same part of the fundus can always be imaged. The part can always be tracked when the defined value x in Step 313 is 0.

Figure 6:
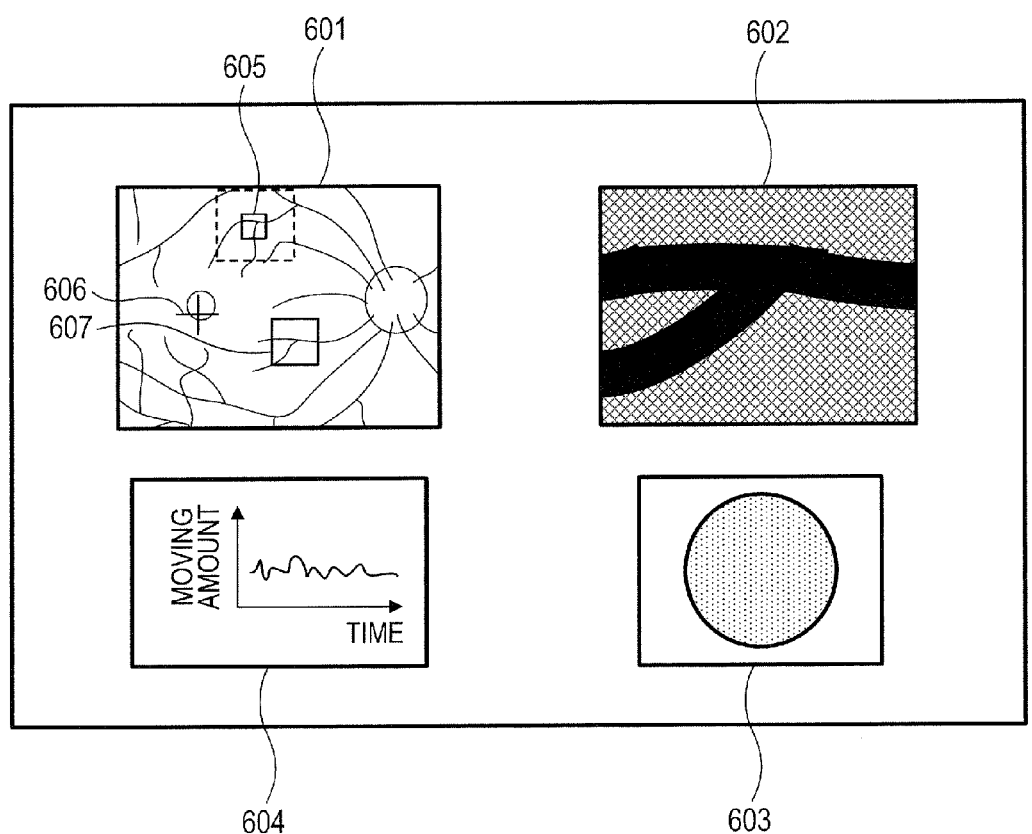
FIG. 6 is a schematic diagram of a GUI according to the first embodiment.

While the AO-SLO image is acquired, the tracking is performed so that an image of a desired position may be acquired. This enables photoreceptor analysis by superimposition of images, and bloodstream analysis by monitoring blood vessels. During imaging, images as illustrated in FIG. 6 are displayed on the display device 212. A most recent tracking image 605, a most recent image 607 taken by the AO-SLO apparatus, and a fixation target position 606 are displayed on an initially-acquired SLO image 601 in the same screen, and a graph 604 of the moving amount of the eyeball, wavefront sensor information 603, and an AO-SLO image 602 are displayed on the display device. In this embodiment, as a method of displaying the most recent information, the initially-acquired SLO image 601, which is acquired of a wide angle of view, and the fixation target position 606 are displayed while being moved along with the moving of the eyeball. As the display method, there may be employed a display method involving moving the most-recent tracking image 605 and the AO-SLO image on the SLO image 601 of the wide angle of view.

As described above, by dividing the image acquiring area, duplicate irradiation of the same part with beams is eliminated even when the moving of the eye to be inspected is tracked, with the result that the load on the eye to be inspected may be made small and a high-quality AO-SLO image may be acquired.

Second Embodiment

Now, a second embodiment of the present invention is described.

In this embodiment, description is given of an example in which a first fundus imaging apparatus is used as a tracking apparatus and a second fundus imaging apparatus is used as an OCT apparatus, to thereby acquire a stable and high-quality OCT image.

(Overall Configuration of Apparatus)

The fundus imaging apparatus according to this embodiment is described with reference to an optical schematic diagram of FIG. 7.

The first fundus imaging apparatus and the internal fixation target apparatus are similar to those in the first embodiment, and hence description thereof is omitted.

Figure 7:
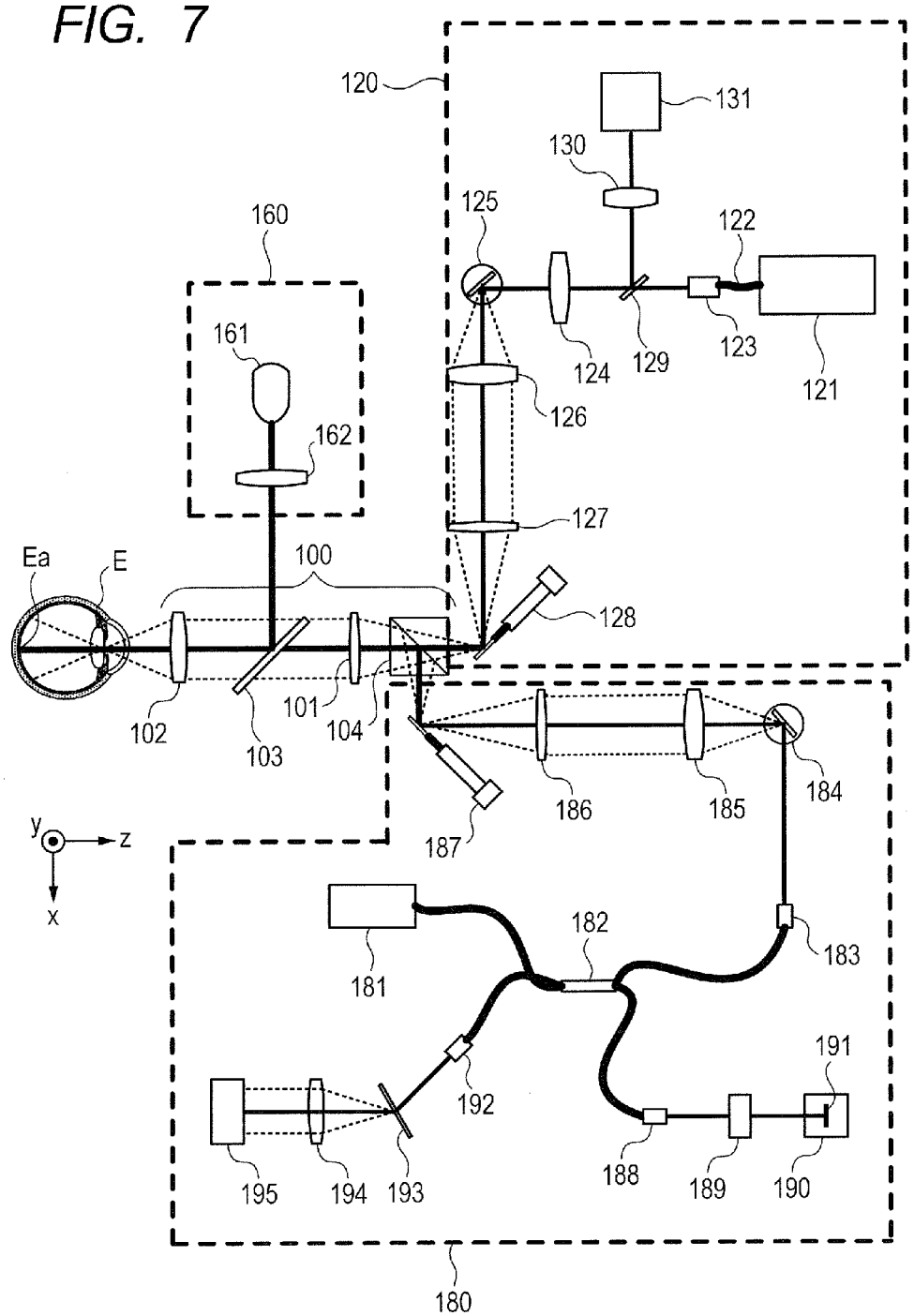
FIG. 7 is a schematic diagram of a configuration of a fundus imaging apparatus according to a second embodiment.

As illustrated in FIG. 7, an OCT apparatus 180 serving as the second fundus imaging apparatus includes a light source 181. As the light source 181, a super luminescent diode (SLD) light source having a center wavelength of 840 nm and a full-width half-maximum wavelength of 45 nm is used. Other than the SLD light source, an amplified spontaneous emission (ASE) light source may suitably be used.

As to the wavelength, wavelengths in the vicinity of 850 nm and 1,050 nm are suitably used for the fundus imaging. Low coherent light radiated from the light source 181 is transmitted through a fiber and enters a fiber coupler 182 to be split to measuring light (also referred to as the OCT beam) and reference light. An interferometer configuration using the fiber is described here, but configuration may be adopted in which a beam splitter is used in a spatial optical system. The measuring light is emitted from a fiber collimator 183 as collimated light.

The measuring light is transmitted through an OCT scanner (Y) 184 and relay lenses 185 and 186, and further through an OCT scanner (X) 187, and enters the eye to be inspected E through the beam splitter 104, the scan lens 101, the dichroic mirror 103, and the ocular lens 102. The beam diameter of the measuring light is about 20 μm at the fundus. In this case, galvano scanners are used as the OCT scanners (X) 187 and (Y) 184.

The measuring light that has entered the eye to be inspected E is reflected by the fundus Ea and follows the same optical path to return to the fiber coupler 182. On the other hand, the reference light is guided from the fiber coupler 182 to a fiber collimator 188 to be radiated as collimated light. The radiated reference light is transmitted through a dispersion compensation glass 189 to be reflected by a reference mirror 191 on a stage with a variable optical path length 190. The reference light reflected by the reference mirror 191 follows the same optical path to return to the fiber coupler 182. The measuring light and the reference light which have returned are combined by the fiber coupler 182 to be guided to a fiber collimator 192. The combined light is hereinafter referred to as interference light.

The fiber collimator 192, a grating 193, a lens 194, and a line sensor 195 constitute a spectrometer. The interference light is measured by the spectrometer as intensity information for each wavelength. The intensity information for each wavelength measured by the line sensor 195 is transferred to a PC (not shown) to form a tomographic image of the fundus Ea of the eye to be inspected E (the phrase "tomographic image" hereinafter indicates a tomographic image of a retina unless otherwise noted).

(Functional Configuration)

Figure 8:
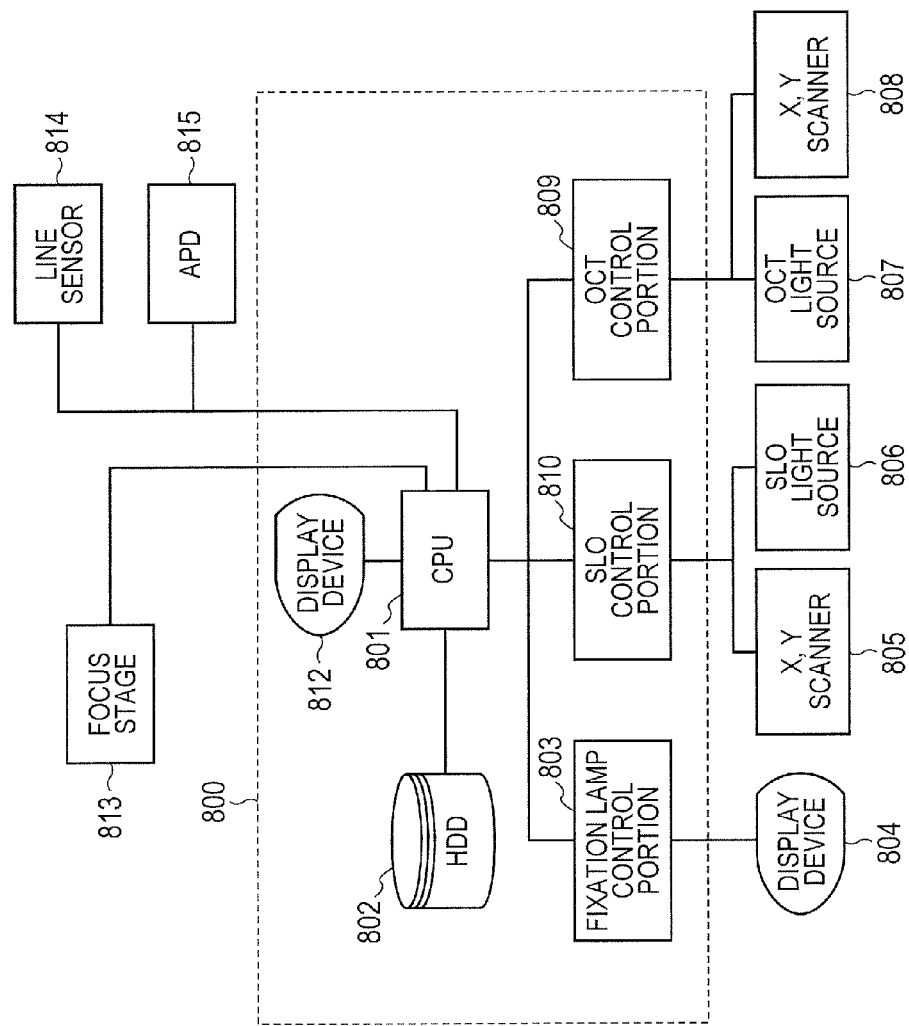
FIG. 8 is a functional schematic diagram of the fundus imaging apparatus according to the second embodiment.

A functional configuration according to this embodiment is described with reference to FIG. 8. A PC 800 for controlling functional members includes a display device 812, a CPU 801, a storage device HDD 802, and a fixation target control portion 803, an SLO control portion 810, and an OCT control portion 809, which are control portions for the respective apparatus. Under instructions from the CPU 801, a display device 804 (corresponding to the light source 161 of FIG. 7) for displaying the fixation target, an X, Y scanner 805 (corresponding to the SLO scanners 125 and 128 of FIG. 7) and an SLO light source 806 (corresponding to the laser light source 121 of FIG. 7) of the SLO apparatus, and an X, Y scanner 808 (corresponding to the OCT scanners 184 and 187 of FIG. 7) and an OCT light source 807 (corresponding to light source 181 of FIG. 7) of the OCT apparatus are operated under the control of the fixation target control portion 803, the SLO control portion 810, and the OCT control portion 809, respectively.

Further, a signal from the eye to be inspected E is obtained via a line sensor 814 (corresponding to the line sensor 195 of FIG. 7), which is a light receiving member of the OCT apparatus, and an APD 815 (corresponding to the APD 131 of FIG. 7), which is a light receiving member of the SLO apparatus. The obtained signal is imaged by the CPU 801 and displayed on the display device 812. In this embodiment, a first image is a tomographic image of the fundus and a second image is a fundus image.

(Flow)

Figure 9:
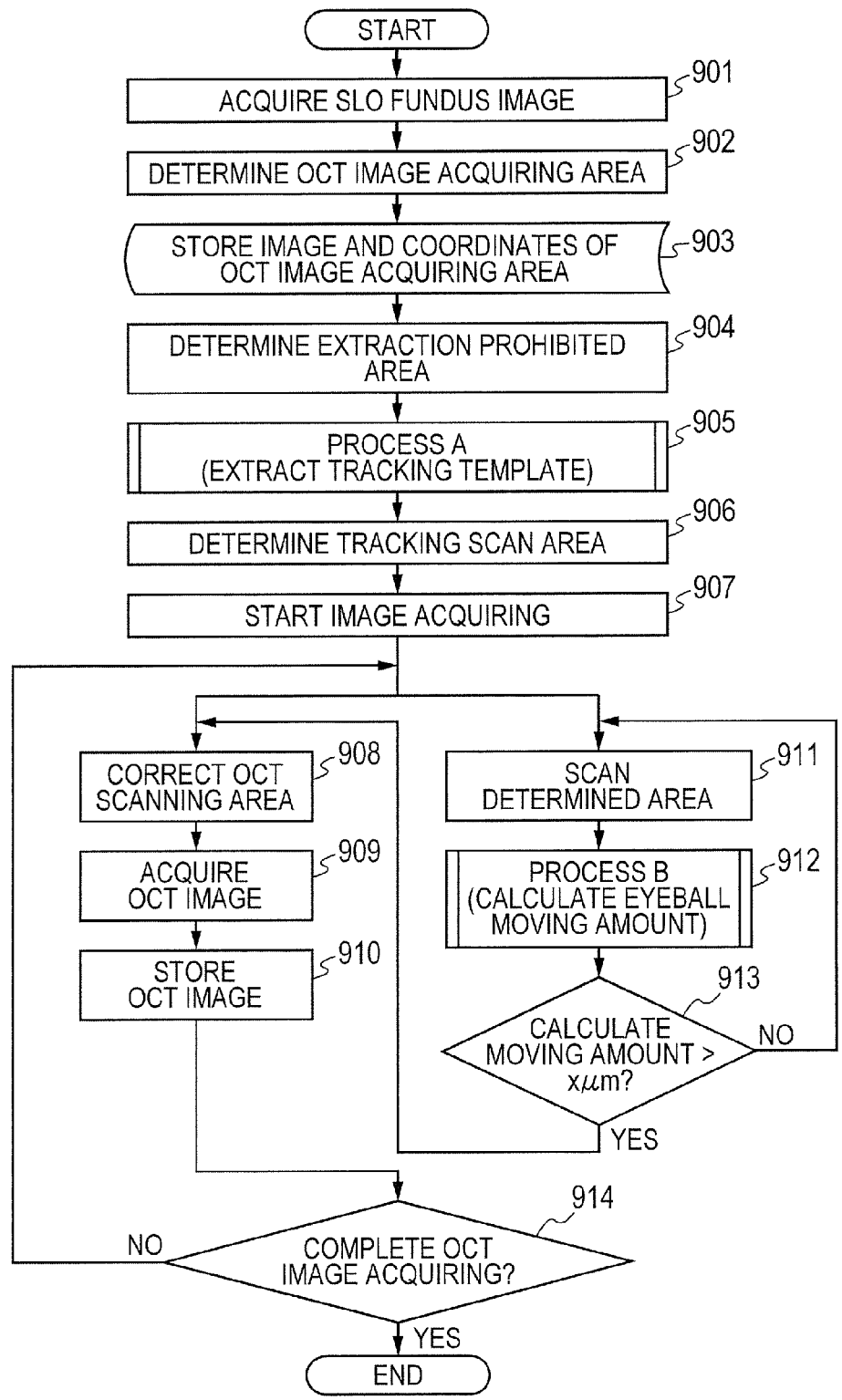
FIG. 9 is a schematic flowchart of a procedure according to the second embodiment.

With the above-mentioned apparatus, the SLO apparatus as the first fundus imaging apparatus is used for tracking and the tracking result is fed back to the scanners of the OCT apparatus, to thereby acquire the OCT image of a desired position stably. A flow thereof is illustrated in FIG. 9. Note that, unless otherwise noted, the processing is executed by the CPU 801.

First, the first fundus imaging apparatus acquires an SLO fundus image by outputting a laser from the laser light source 121 and receiving the reflected light by the APD 131 in a state in which the fixation target 161 is turned on to be presented to the eye to be inspected E (Step 901). On the basis of an instruction by an operator from an input device (not shown), an OCT image acquiring area is determined in the SLO image (Step 902). The OCT image acquiring area is stored in a memory of the CPU 801 (Step 903).

An area of 2,000 μm from the OCT image acquiring area is set as a prohibited area of acquisition of the SLO image (Step 904). Outside the prohibited area of the acquisition of the SLO image, at least one template for tracking is extracted (process A: Step 905). An area of 500 μm in the periphery of the extracted template is determined as a tracking scan area (Step 906). Imaging for the fundus image for diagnosis is started (Step 907), and the OCT apparatus and the SLO apparatus are operated. The OCT apparatus drives the X, Y scanner 808 to scan the image acquiring area determined in Step 902 (Step 908), and an OCT signal is acquired to be imaged (Step 909). The OCT image is stored in the HDD 802 (Step 910).

At the same time, the X, Y scanner 805 of the SLO apparatus is used to scan the area determined in Step 906 (Step 911), to thereby acquire the SLO image. Template matching is executed in the acquired SLO image and coordinates of the template are compared with matching coordinates to calculate eyeball moving (moving amount and direction) (process B: Step 912). When the moving amount does not exceed a defined value (x), the processing returns to Step 911, and when the moving amount exceeds the defined value, the moving amount is reflected in driving the scanner of the OCT apparatus (Yes in Step 913). When the OCT image acquiring is complete, the processing is ended (Yes in Step 914).

The process A and the process B are the same as those in the first embodiment, and hence description thereof is omitted.

Specific Example

Figure 10A:
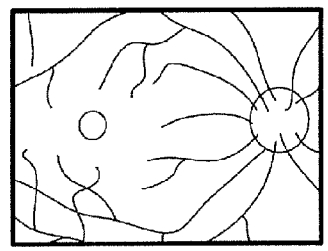
FIGS. 10A, 10B, 10C, 10D, 10E and 10F are explanatory diagrams of specific fundus images according to the second embodiment.

A specific example is described with reference to FIGS. 10A to 10F. The first fundus imaging apparatus causes a beam of 780 nm to enter the retinal fundus, and uses the galvano scanners 125 and 128 to scan an area of 10 mm×8 mm on the fundus with a spot diameter of 20 μm. A signal obtained by the APD 131 is imaged by the PC 800. FIG. 10A is a schematic diagram of the image. In the obtained SLO image of FIG. 10A, the macula, the optic disc, and a vascular image may be observed as in the first embodiment.

Figure 10B:
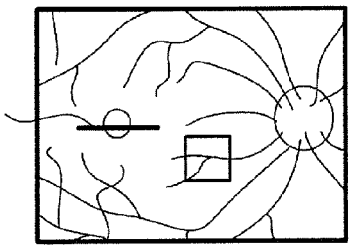
Figure 10C:
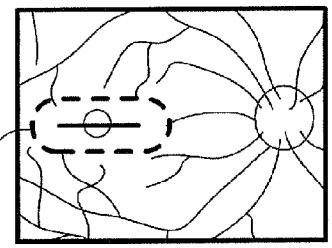

An image area 1002 desired to be imaged by the OCT apparatus as the second fundus imaging apparatus is determined as specified by the operator (FIG. 10B). In the OCT image acquiring in this embodiment, B-scan of the same part is performed multiple times to acquire multiple OCT images, and the multiple OCT images are superimposed on each other, to thereby acquire a high-quality image. An OCT image acquiring area is 4 mm. Next, in order to place no load on the eye to be inspected and take the eyeball moving amount into consideration, an area of 2 mm in the periphery of the OCT image acquiring area is specified as a tracking template extraction prohibited area 1003 (FIG. 10C).

Figure 10D:
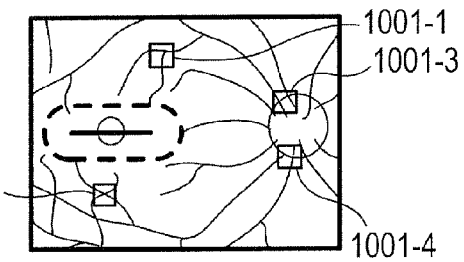
Figure 10E:
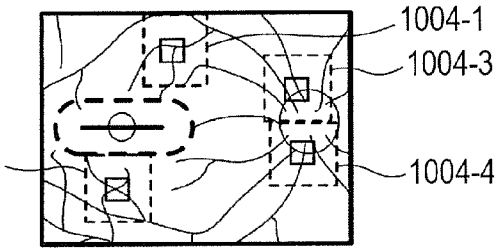

Next, in order to perform tracking, templates are extracted from the SLO image of FIG. 10A. In the extraction, the templates are extracted within the area of the SLO image of FIG. 10A other than the area 1003 (FIG. 10D). Vessel bifurcation areas are extracted as template images 1001-1 to 1001-4. The size of each template is 0.5 mm×0.5 mm. Each template moves with eyeball movements, and hence with the addition of 1 mm to the periphery of each template, scan areas 1004-1 to 1004-4 of the templates are each 1.5 mm×1.5 mm (FIG. 10E).

Figure 10F:
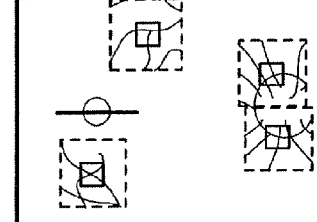

When the OCT image is actually acquired while tracking is performed, the image as illustrated in FIG. 10F is obtained. The acquired SLO image is searched for the same images as the extracted template images 1001-1 to 1001-4. Image areas with the highest match rates of the respective templates are identified and compared with the template coordinates to calculate the moving of the fundus. With the tracking speed being 50 Hz and the acquisition speed of the OCT image being 70 Hz, control is performed so that the same part of the fundus can be imaged as much as possible. The defined value x in Step 913 is 30 μm. The defined value x is 30 μm in this embodiment, but speckle after the superimposition may be addressed by changing x by the beam diameter.

Figure 11:
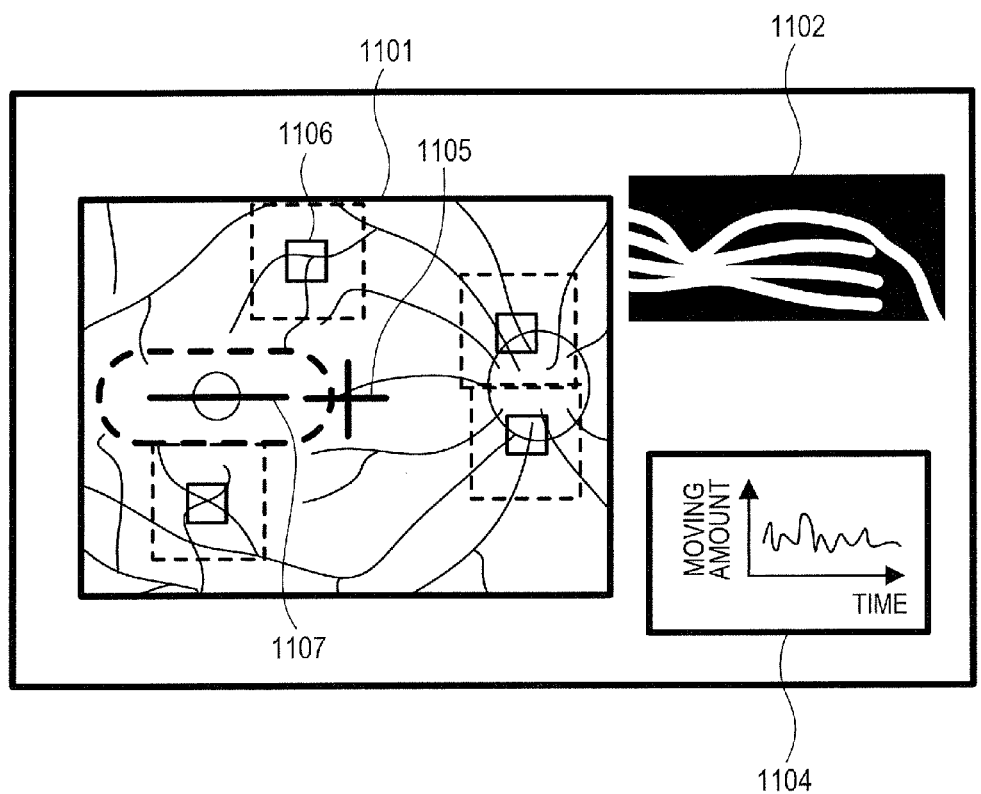
FIG. 11 is a schematic diagram of a GUI according to the second embodiment.

While the OCT image is acquired, the tracking is performed so that an image of a desired position may be acquired. This enables acquisition of a high-quality OCT image by superimposition of images and a three-dimensional OCT image at the same interval. During imaging, images as illustrated in FIG. 11 are displayed on the display device 812. Control is performed so that most recent tracking information 1106, an OCT image acquiring area 1107, and a fixation target position 1105 on an acquired SLO image 1101, a graph 1104 of the moving amount of the eyeball, and an OCT image 1102 are displayed on the display device.

As described above, with the use of different image acquiring areas, a high-quality OCT image with small load on the eye to be inspected may be acquired.

Another Embodiment

In the above-mentioned embodiments, the apparatus to which the moving of the eye is fed back may be an OCT apparatus such as an SD-OCT or SS-OCT apparatus, an AO-SLO apparatus, or an ophthalmologic apparatus for perimetry, blood flow measurement, or the like. Further, ophthalmologic equipment is corrected in real time for the moving of the eye. However, data of the moving may be stored, and the images and the measured positions may be registered after the measurement of the moving of the eye is complete.

In this embodiment, the image acquiring area is controlled by the scanners. However, in a case where a low tracking speed may suffice, the scan position may be defined by ON/OFF control in which the entire fundus is scanned and the beam is turned OFF only in a part where another beam overlaps.

Moreover, in this embodiment, the SLO apparatus is used as the tracking apparatus. However, a line-SLO apparatus, which irradiates the fundus with a line beam, may provide a similar effect by performing ON/OFF control of a scan or beam partially. Moreover, the tracking apparatus detects the cycloduction or the like. Therefore, in a case where multiple template images are to be extracted, the template images are extracted so as not to overlap with the beam of the second fundus imaging apparatus, or when overlapped, the template images are extracted at different timing, with the result that a similar effect may be provided.

Further, in the above-mentioned embodiments, the AO-SLO apparatus is used in forming the image, but the present invention is not limited thereto. Specifically, the OCT apparatus is used instead so that a so-called two-dimensional pseudo SLO image, which is obtained by integrating in a depth direction an OCT image acquired by the OCT apparatus, is used and the first area may be corrected on the basis of the image. Further, it is also possible to determine an OCT image in a time division manner and use the OCT image. Moreover, a monochrome image, which is obtained with IR as scanning light, may be used to determine whether or not the correction is required.

Other Embodiments

Further, the present invention can also be realized by performing the following processing. That is, the processing involves supplying software (program) for realizing the functions of the above-mentioned embodiments to a system or an apparatus via a network or various storage media and causing a computer (or a CPU, an MPU, or the like) of the system or the apparatus to read and execute the program.

Note that, the present invention is not limited to the above-mentioned embodiments and can be variously modified or changed without departing from the spirit of the present invention. For example, in the above-mentioned embodiments, the case where an object to be inspected is an eye has been described, but the present invention can also be applied to objects to be measured such as a skin and an organ other than an eye. In this case, the present invention has an embodiment mode as medical equipment such as an endoscope other than an ophthalmologic apparatus. Thus, it is preferred that the present invention be understood as an inspecting apparatus exemplified by an ophthalmologic apparatus and the eye to be inspected be understood as an embodiment mode of an object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-053316, filed Feb. 21, 2012, which is hereby incorporated by reference herein in its entirety.

What is claimed is:

1. An imaging apparatus for imaging a first fundus image of a first area of an eye to be inspected in accordance with return light from the first area, which is irradiated with first light emitted from a first light source, the imaging apparatus comprising:
   a setting unit that sets the first area of the eye to be inspected;
   a determination unit that determines, in accordance with the first area, a prohibited area of acquisition of a second fundus image, wherein the prohibited area is an area which is not irradiated with second light emitted from a second light source when the first area is irradiated with the first light;
   a detection unit that detects moving of the eye to be inspected in accordance with the second fundus image, which is generated by using return light from a second area, other than the prohibited area which is not irradiated with the second light, the second area being irradiated with the second light;
   a correction unit that corrects the first area in accordance with the detected moving of the eye to be inspected; and
   a forming unit that forms a first fundus image of the eye to be inspected in accordance with the return light from the corrected first area, which is irradiated with the first light,
   wherein the second light source is different from the first light source,
   wherein the first light enters the eye to be inspected after the first area is set by the setting unit, and
   wherein the setting unit, the determination unit, the detection unit, the correction unit, and the forming unit are implemented using a processor executing a program.

2. An imaging apparatus according to claim 1, wherein the determination unit determines, as the prohibited area, an area obtained by adding a predetermined amount to the periphery of the first area of the eye to be inspected.

3. An imaging apparatus according to claim 1, further comprising a forming unit that forms a plurality of second fundus images for detecting moving of the eye to be inspected at different times in accordance with the return light from the second area, which is irradiated with the second light,
   wherein the detection unit detects the moving of the eye to be inspected in accordance with the plurality of second fundus images.

4. An imaging apparatus according to claim 3, further comprising a unit that extracts a characteristic image from each of the plurality of second fundus images for detecting moving of the plurality of second fundus images,
   wherein the detection unit detects the moving of the eye to be inspected by comparing a newly-formed second fundus image and the extracted characteristic image.

5. An imaging apparatus according to claim 3, wherein a resolution of the first fundus image is higher than resolutions of the plurality of second fundus images.

6. An imaging apparatus according to claim 1, further comprising:
   a first scanning unit that scans the first area with the first light; and
   a second scanning unit that scans the second area with the second light,
   wherein the correction unit corrects a scan area of the first scanning unit.

7. An imaging apparatus according to claim 1, wherein the imaging apparatus further comprises an acquisition unit that acquires the second fundus image, and
    wherein the setting unit sets the first area on the second fundus image acquired by the acquisition unit when the first light does not enter the eye.

8. An imaging apparatus according to claim 1, wherein the first fundus image formed by the forming unit comprises at least one of a fundus image and a fundus tomographic image.

9. An imaging apparatus according to claim 1, wherein the first fundus image comprises a SLO fundus image, and
    wherein the second fundus image comprises a SLO fundus image.

10. An imaging apparatus according to claim 9, wherein the corrected first area is an area in the eye to be inspected that is different from the first area.

11. An imaging apparatus according to claim 9, wherein correction unit corrects the first area by changing a scan area.

12. An imaging apparatus according to claim 1, wherein the first image comprises an AO-SLO image, and
    wherein the second image comprises an SLO image, and
    wherein the corrected first area is an area in the eye that is different from the first area.

13. An imaging method of imaging a first fundus image of a first area of an eye to be inspected in accordance with return light from the first area, which is irradiated with first light emitted from a first light source, the imaging method comprising:
    setting the first area of the eye to be inspected;
    determining, in accordance with the first area, a prohibited area of acquisition of a second fundus image, wherein the prohibited area is an area which is not irradiated with second light emitted from a second light source when the first area is irradiated with the first light, wherein the second light source is different from the first light source;
    detecting moving of the eye to be inspected in accordance with the second fundus image, which is generated by using return light from a second area, other than the prohibited area which is not irradiated with the second light, wherein the second area is irradiated with the second light, and wherein the first light enters the eye to be inspected after the first area is set in the setting step;
    correcting the first area in accordance with the detected moving; and
    forming a first fundus image of the eye to be inspected in accordance with the return light from the corrected first area, which is irradiated with the first light.

14. An imaging method according to claim 13, wherein the determination step comprises determining, as the prohibited area, an area obtained by adding a predetermined amount to the periphery of the first area of the eye to be inspected.

15. An imaging method according to claim 13, further comprising a forming step of forming a plurality of second fundus images for detecting moving of the eye to be inspected at different times in accordance with the return light from the second area, which is irradiated with the second light,
    wherein the detection step comprises detecting the moving of the eye to be inspected in accordance with the plurality of second fundus images.

16. A program for causing a computer to execute the steps of the imaging method according to claim 13.

17. An imaging apparatus for detecting moving of an eye to be inspected, for correcting a first area of the eye to be inspected which is irradiated with first light in accordance with the detected moving, and for forming a first image of the eye to be inspected in accordance with return light from the corrected first area, the apparatus comprising:
    an imaging unit that acquires an image of the eye to be inspected having a wider angle than the first image;
    a determination unit that determines, in accordance with the first area, a prohibited area of acquisition of a second image, wherein the prohibited area is an area which is not irradiated with second light when the first area is irradiated with the first light; and
    a detecting unit that detects the moving of the eye to be inspected in accordance with (1) a second image, generated by using return light from a second area which is irradiated with the second light, that is acquired and (2) the wider-angle image, wherein the second area is an area other than the prohibited area from an entire area of the wider-angle image,
    wherein the determination unit and the detecting unit are implemented using a processor executing a program, and
    wherein the first area is corrected in accordance with the detected moving.

18. An imaging apparatus according to claim 17, wherein the detecting unit detects the moving of eye to be inspected whenever the first image is formed.

19. An imaging apparatus according to claim 17, wherein the determination unit determines, as the prohibited area, an area obtained by adding a predetermined amount to the periphery of the first area in the wider-angle image.

20. An imaging apparatus according to claim 17, wherein the first image is an AO-SLO image or a tomographic image, and
    wherein the second image is an SLO image.

21. An imaging method of detecting moving of an eye to be inspected, of correcting a first area of the eye to be inspected which is irradiated with first light in accordance with the detected moving, and of forming a first image of the eye to be inspected in accordance with return light from the corrected first area, the method comprising:
    acquiring an image of the eye to be inspected having a wider angle than the first image;
    determining, in accordance with the first area, a prohibited area of acquisition of a second image, wherein the prohibited area is an area which is not irradiated with second light the first area is irradiated with the first light; and
    detecting the moving of the eye to be inspected in accordance with (1) a second image, generated by using return light from a second area which is irradiated with the second light, that is acquired and (2) the wider-angle image, wherein the second area is an area other than the prohibited area from the entire area of the wider-angle image,
    wherein the first area is corrected in accordance with the detected moving.

* * * * *